United States Patent [19]
Morrissey

[11] Patent Number: 5,967,780
[45] Date of Patent: Oct. 19, 1999

[54] DENTAL VACUUM RECEPTACLE AND METHOD

[76] Inventor: Donald J. Morrissey, 7255 Juniper Dr., Colorado Springs, Colo. 80908

[21] Appl. No.: 08/991,951

[22] Filed: Dec. 16, 1997

[51] Int. Cl.⁶ ............................. A61C 17/06; A61C 17/14
[52] U.S. Cl. .............................................. 433/92; 159/25.2
[58] Field of Search ............................. 433/92; 159/25.2, 159/28.4, 43.1, 47.3, 6.2; 422/309, 105, 106, 119

[56] References Cited

U.S. PATENT DOCUMENTS

| | | | |
|---|---|---|---|
| 3,746,033 | 7/1973 | Keiper, II | 137/205 |
| 4,356,959 | 11/1982 | Rosander | 494/60 |
| 4,386,910 | 6/1983 | Cattani | 433/92 |
| 4,529,383 | 7/1985 | Jerzy | 433/92 |
| 4,564,374 | 1/1986 | Hofmann | 95/24 |
| 4,580,978 | 4/1986 | Motola et al. | 433/92 |
| 5,741,397 | 4/1998 | Kraver | 433/92 X |
| 5,797,742 | 8/1998 | Fraker | 433/92 |

Primary Examiner—Nicholas D. Lucchesi
Attorney, Agent, or Firm—Richard W. Hanes

[57] ABSTRACT

A vacuum receptacle and method is provided for accumulating, holding and disposing of liquids and certain solids that are withdrawn from the mouths of dental patients by a suction tube or other apparatus placed in the patient's mouth during dental procedures. The receptacle incorporates a vacuum outlet port to which a vacuum pump line is attached. The vacuum pump line pulls air and dental debris through the receptacle from a waste inlet port which is connected through a hose to the tube in the patient's mouth. A baffle is provided to impact and decelerate the dental debris as it enters the receptacle. Once decelerated, the dental debris falls to the bottom of the receptacle where it accumulates up to a predetermined level whereupon a float assembly activates a discharge pump. The discharge pump is connected to a waste outlet port that removes the accumulated fluid waste via an internal waste outlet tube. In the event the float assembly or discharge pump fails and the waste in the canister continues to accumulate, a vacuum safety float assembly is activated by the rising waste. Upon activation, the safety float assembly temporarily disables the vacuum pump thereby preventing further accumulation.

15 Claims, 2 Drawing Sheets

DENTAL VACUUM RECEPTACLE AND METHOD

FIELD OF INVENTION

The present invention relates to dental station accessories and, in particular, to an improved vacuum receptacle and method that enables accumulation, holding and disposal of liquid and certain solids withdrawn from dental patient mouths.

BACKGROUND OF THE INVENTION

Heretofore, vacuum systems that have been utilized in extracting the liquid and debris from dental patient's mouth or from another source during a dental procedure have posed several problems for the dental practitioner. Among these problems are the wastefulness and untimeliness involved in disposing of the liquid and debris. In some systems, running water is utilized to establish a vacuum which is directed to the place to be evacuated such as the patient's mouth and which extracts the liquid and dental debris therefrom and transports it to the vacuum source which, in this case, is the continually running water. A significant disadvantage of such a system is that a very large amount of water must be utilized during the continuous operation of the system which must then be discarded. Since the water which operates the system must be discarded during its use and may contain deleterious matter in the form of dental debris, significant environmental problems may arise. Obviously, one such environmental problem is the high rate of water usage during operation.

Other systems, while not employing continually running water as a vacuum source, nonetheless utilize a centrally-located debris canister or variant thereof wherein the extracted debris is collected during operation. Such a debris canister must periodically be emptied and, as a result, the centrally-located system must be shut down at that time. Such a system can present a significant problem when the canister must be emptied while the dentist is performing a dental procedure on a patient. Some systems incorporate mechanisms which are able to sense the moment of need for emptying the debris canister and are further capable of disposing of the contents therein. However, such systems most often require installation in close proximity to a floor drain which can be impractical or impossible. Additionally, even if floor drain access is practical, these systems fail to collect and accumulate particulate solid waste, allowing same to enter the drain creating the potential for future plumbing problems.

Common to each of the aforementioned dental vacuum systems is the problem associated with obtaining optimal dental waste mass flow rates while minimizing both negative vacuum pressures necessary for such flow rates and facility space needed for locating the vacuum canisters. The optimal dental waste mass flow rate is approximately five cubic feet per minute. Heretofore, such a mass flow rate was obtainable only when 40–55 gallon debris canisters and their associated high required negative vacuum pressures were used in conjunction therewith. Such is the case because prior art systems have no means of decelerating the entering debris, such that as the volume of the canister used decreases, the likelihood of the debris being undesirably sucked into the vacuum pump line increases. Thus, when smaller debris canisters were used, the maximum available mass flow rates declined correspondingly.

Additionally, installation or removal of the prior art dental vacuum systems requires considerable plumbing and property improvements to access the required water, vacuum lines and electricity. In such a case, the considerable inconvenience and expense incurred by the dental professional are obvious.

What is needed in the art is an improved dental vacuum receptacle that is independently operable at individual dental treatment stations, accumulates liquid and solid waste from dental procedures and facilitates pumping of this waste out to an overhead plumbing system at such time as the quantity of waste demands. The receptacle should also access any necessary water, electricity and waste removal from overhead utility access thereby permitting expeditious and convenient installation while minimizing or eliminating the need for altering the structure within which the receptacle is used. In addition, the system should enable optimal dental waste mass flow rates while drastically reducing both negative vacuum pressures needed to obtain such flow rates and facility space needed for locating the vacuum canisters.

The present invention accomplishes these objectives by providing a vacuum receptacle that accumulates and holds liquids and certain solids that are withdrawn from the mouths of dental patients by a suction tube or other apparatus placed in the patient's mouth during dental procedures. The receptacle incorporates a vacuum outlet port to which a vacuum pump line is attached. The vacuum pump line pulls air through the receptacle from a waste inlet port which is connected through a hose to the tube in the patient's mouth. Along with the air coming into the receptacle through the waste inlet port is the fluid and solid sediment debris from the patient's mouth. In order to improve the dental waste mass flow rate capability of the receptacle and to prevent suction of the fluid and sediments into the vacuum pump line, a baffling system is provided to impact and decelerate the fluids and sediments as they enter the receptacle. Once decelerated, the fluid and sediments fall to the bottom of the receptacle where they accumulate up to a predetermined level whereupon a float assembly activates a discharge pump. The discharge pump is connected to a waste outlet port that removes the accumulated fluids via an internal waste outlet tube. The sediment is collected at the bottom of the receptacle whereupon the sediment may be periodically disposed of as solid waste, thereby minimizing, if not eliminating the threat of plumbing damage. In the event the float assembly or discharge pump fails and the waste in the canister continues to accumulate, a vacuum safety float assembly is activated by the rising waste. Upon activation, the safety float assembly temporarily disables the vacuum pump thereby preventing further accumulation.

Listed below are samples of patents based in part on dental suction devices. These patents are merely representative of the art and do not suggest the teachings of the present invention:

U.S. Pat. No. 3,746,033 (1973) to Keiper, II discloses a dental oral evacuating system which includes a receptacle unit through which liquid and solid waste material passes after withdrawal from the oral cavity and means to connect the receptacle to a source of flushing liquid for said receptacle.

U.S. Pat. No. 4,356,959 (1982) to Rosander discloses an apparatus for separating solid particles, particularly mercury compounds and alloys, from a fluid, such as dental waste water, contaminated therewith.

U.S. Pat. No. 4,386,910 (1983) to Cattani discloses a console specifically designed for the suction tubes of suction units used in dentistry.

U.S. Pat. No. 4,529,383 (1985) to Jerzy discloses a gravity separator intended for use in dental suction apparatus comprising at least one sucker having a suction mouthpiece and a sucker line.

U.S. Pat. No. 4,564,374 (1986) to Hofmann discloses a separator for incorporation into dental suction apparatus for separating from the suction stream liquid and solid materials coming from the mouth of a patient.

U.S. Pat. No. 4,580,978 (1986) to Motola et al. discloses a vacuum operated dental evacuation system.

SUMMARY OF THE INVENTION

The primary aspect of the present invention is to provide an improved dental vacuum receptacle that is independently operable at individual dental treatment stations, accumulates liquid and solid sediment waste from dental procedures and facilitates pumping of the fluid out to an overhead plumbing system and disposal of the sediment waste as solid waste at such time as the quantity of waste demands.

Another aspect of the present invention is to provide an improved dental vacuum receptacle that accesses any necessary water, electricity and waste removal from overhead utility access thereby permitting expeditious and convenient installation while minimizing or eliminating the need for altering the structure within which the receptacle is used.

Another aspect of the present invention is to provide an improved dental vacuum receptacle that enables optimal dental waste mass flow rates while drastically reducing both negative vacuum pressures needed to obtain such flow rates and facility space needed for locating the vacuum canisters.

Another aspect of the present invention is to provide a method of conveniently and automatically disposing of dental waste while minimizing or eliminating the need for altering the structure within which the method is practiced.

Additional aspects, advantages and novel features of the invention will be set forth in part in the description which follows, and in part will become apparent to those skilled in the art upon examination of the following or may be learned by practice of the invention. The aspects and advantages of the invention may be realized and attained by means of the instrumentalities and combinations particularly pointed out in the appended claims.

The present invention provides a vacuum receptacle that accumulates and holds liquids and certain solids that are withdrawn from the mouths of dental patients by a suction tube or other apparatus placed in the patient's mouth during dental procedures. The receptacle incorporates a vacuum outlet port to which a vacuum pump line is attached. The vacuum pump line pulls air through the receptacle from a waste inlet port which is connected through a hose to the tube in the patient's mouth. Along with the air coming into the receptacle through the waste inlet port are the fluid and solid sediment debris from the patient's mouth. In order to improve the dental waste mass flow rate capability of the receptacle and to prevent suction of the fluid and sediments into the vacuum pump line, a baffling system is provided to impact and decelerate the fluids and sediments as they enter the receptacle. Once decelerated, the fluid and sediments fall to the bottom of the receptacle where they accumulate up to a predetermined level whereupon a float assembly activates a discharge pump. The discharge pump is connected to a waste outlet port that removes the accumulated fluids via an internal waste outlet tube. The sediment is collected at the bottom of the receptacle whereupon the sediment may be periodically disposed of as solid waste, thereby minimizing, if not eliminating the threat of plumbing damage. In the event the float assembly or discharge pump fails and the waste in the canister continues to accumulate, a vacuum safety float assembly is activated by the rising waste. Upon activation, the safety float assembly temporarily disables the vacuum pump thereby preventing further accumulation.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1:
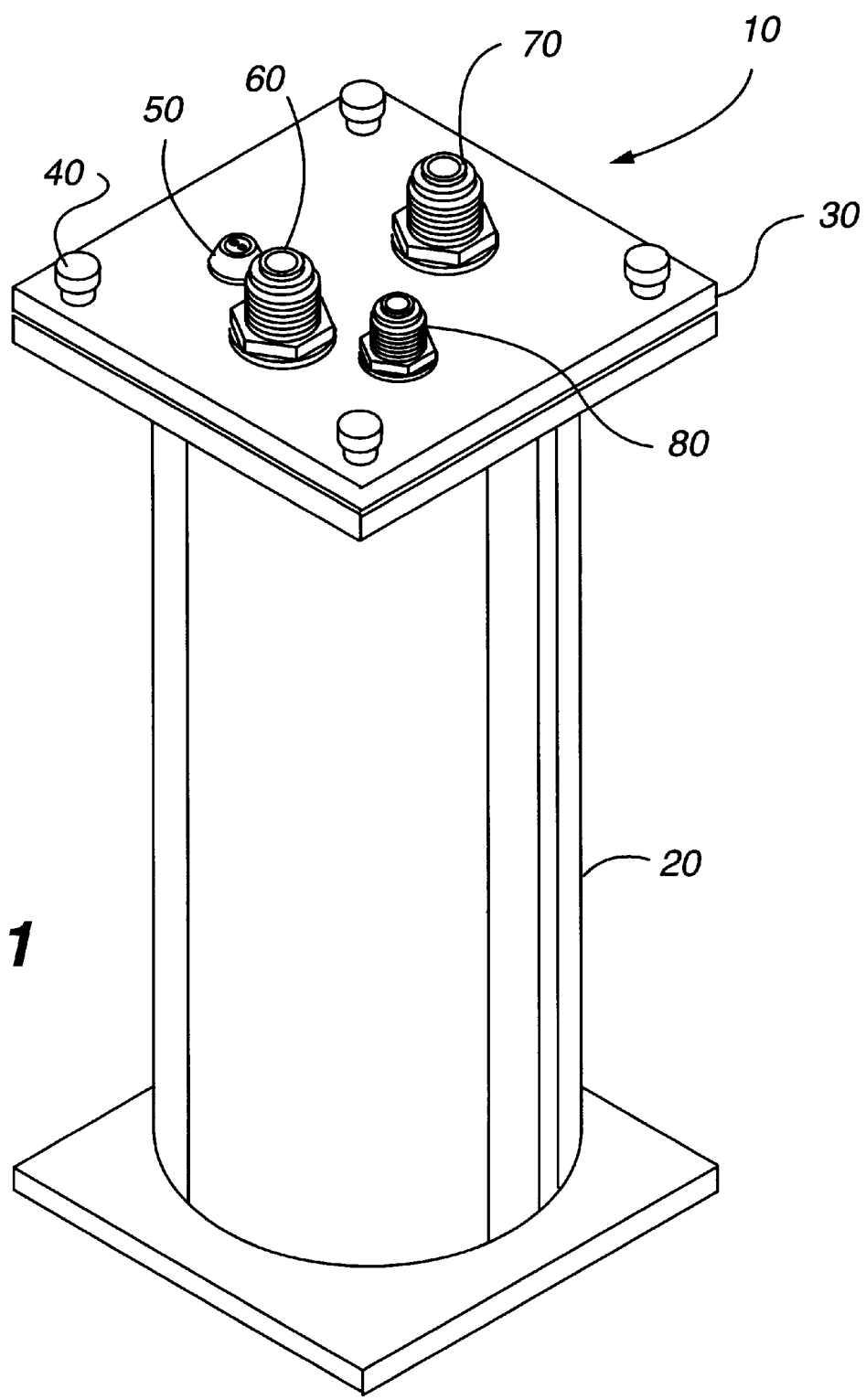
FIG. 1 is a top perspective view of the preferred embodiment improved dental vacuum receptacle.

Referring to FIG. 1 a dental vacuum receptacle 10 is comprised of a vacuum canister 20 with a lid 30 situated thereon and removably fastened to the vacuum canister 20 by lid retainers 40. Disposed upon the lid 30 and allowing internal access to the vacuum canister 20 are waste level switch fitting 50, vacuum outlet port 60, waste inlet port 70, and waste outlet port 80.

Figure 2:
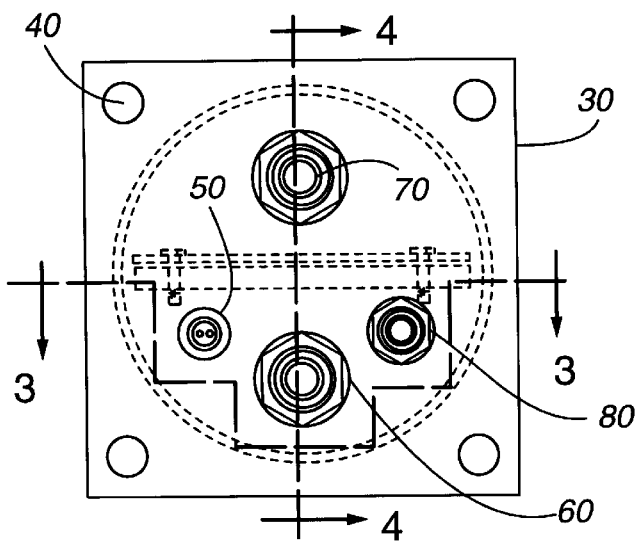
FIG. 2 is a top view of the preferred embodiment improved dental vacuum receptacle.

Referring next to FIG. 2 shown is lid 30 and lid retainers 40. Disposed upon the lid 30 are waste level switch fitting 50, vacuum outlet port 60, waste inlet port 70, and waste outlet port 80.

Figure 3:
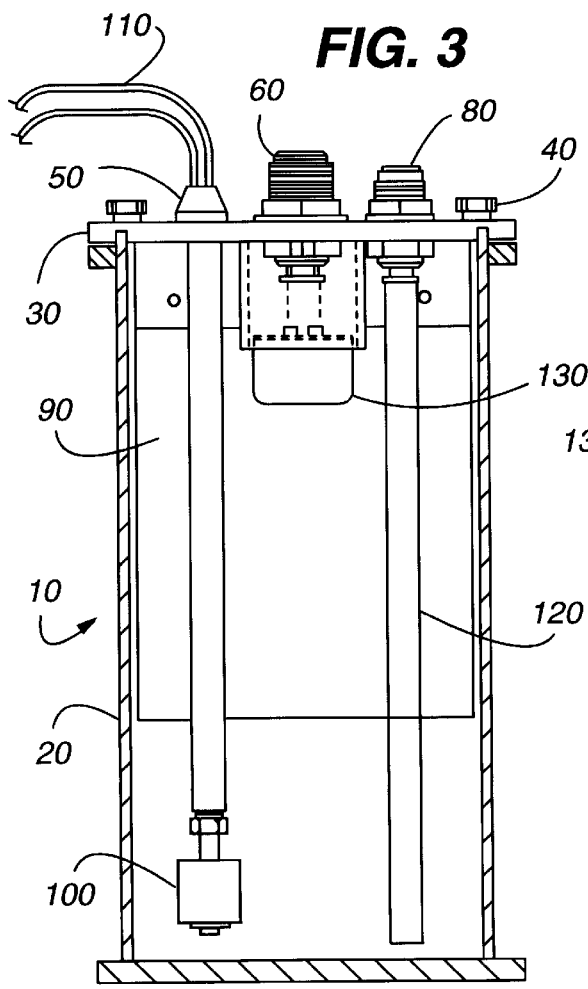
FIG. 3 is a side sectional view of the preferred embodiment improved dental vacuum receptacle along broken line 3 of FIG. 2.

Referring next to FIG. 3 a dental vacuum receptacle 10 is comprised of a vacuum canister 20 with a lid 30 situated thereon and removably fastened to the vacuum canister 20 by lid retainers 40. Disposed upon the lid 30 and allowing internal access to the vacuum canister 20 are waste level switch fitting 50, vacuum outlet port 60, waste inlet port (not shown), and waste outlet port 80. A vacuum pump line (not shown) is attached to vacuum outlet port 60. The vacuum pump line pulls air through the vacuum canister 20 from the waste inlet port which is connected through a hose (not shown) to a tube in a patient's mouth. Along with the air coming into the vacuum canister 20 through the waste inlet port are fluid and solid sediment debris from the patient's mouth. The fluid and sediments are released into the vacuum canister 20 through a waste inlet discharge tube (not shown) and are impacted and decelerated by a waste inlet discharge shell (not shown). In order to prevent suction of the fluid and sediments into the vacuum pump line, a flat-surfaced baffle plate 90 is provided to further impact and decelerate the fluids and sediments as they enter the vacuum canister 20. Once decelerated, the fluid and sediments fall to the bottom of the vacuum canister 20 where they accumulate up to a predetermined level whereupon a waste level switch assembly 100 activates a discharge pump (not shown) by means of waste level switch wiring 110. The discharge pump is connected to the waste outlet port 80 that removes the accumulated fluids via an internal waste outlet tube 120. In the event the waste level switch assembly 100 or discharge pump fails and the waste in the vacuum canister 20 continues to accumulate, a vacuum safety float assembly 130 is activated by the rising waste. Upon activation, the safety float assembly 130 temporarily disables the vacuum pump thereby preventing further accumulation.

Figure 4:
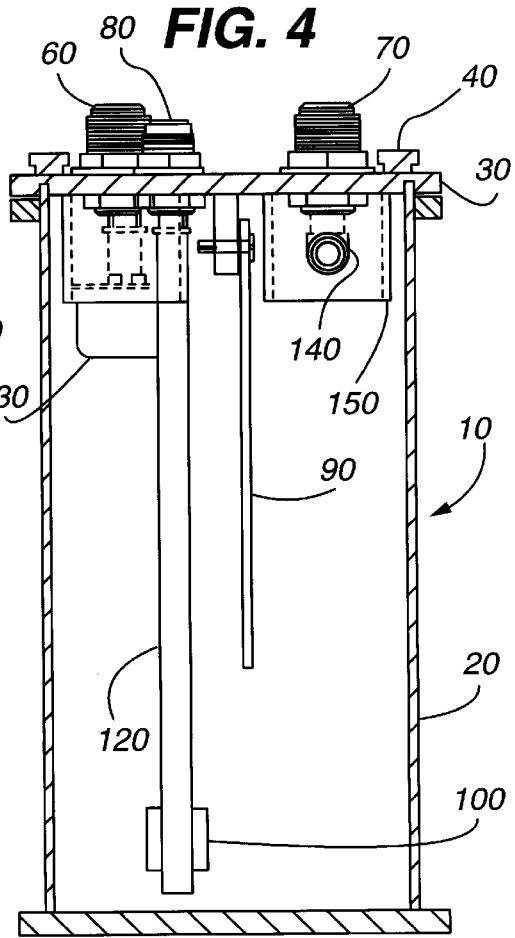
FIG. 4 is a side sectional view of the preferred embodiment improved dental vacuum receptacle along broken line 4 of FIG. 2.

Referring next to FIG. 4 a dental vacuum receptacle 10 is comprised of a vacuum canister 20 with a lid 30 situated thereon and removably fastened to the vacuum canister 20 by lid retainers 40. Disposed upon the lid 30 and allowing internal access to the vacuum canister 20 are waste level switch fitting (not shown), vacuum outlet port 60, waste inlet port 70, and waste outlet port 80. A vacuum pump line (not shown) is attached to vacuum outlet port 60. The vacuum pump line pulls air through the vacuum canister 20 from the waste inlet port 70 which is connected through a hose (not shown) to a tube in a patient's mouth. Along with the air coming into the vacuum canister 20 through the waste inlet port 70 are fluid and solid sediment debris from the patient's mouth. The fluid and sediments are released into the vacuum canister 20 through a waste inlet discharge tube 140 and are impacted and decelerated by a waste inlet discharge shell 150. In order to prevent suction of the fluid and sediments into the vacuum pump line, a flat-surfaced baffle plate 90 is provided to further impact and decelerate the fluids and sediments as they enter the vacuum canister 20. Once decelerated, the fluid and sediments fall to the bottom of the vacuum canister 20 where they accumulate up to a predetermined level whereupon a waste level switch assembly 100 (partially hidden) activates a discharge pump (not shown) by means of waste level switch wiring (not shown). The discharge pump is connected to the waste outlet port 80 that removes the accumulated fluid via an internal waste outlet tube 120. In the event the waste level switch assembly 100 or discharge pump fails and the waste in the vacuum canister 20 continues to accumulate, a vacuum safety float assembly 130 is activated by the rising waste. Upon activation, the safety float assembly 130 temporarily disables the vacuum pump thereby preventing further accumulation.

Although the present invention has been described with reference to preferred embodiments, numerous modifications and variations can be made and still the result will come within the scope of the invention. No limitation with respect to the specific embodiments disclosed herein is intended or should be inferred.

I claim:

1. An improved vacuum receptacle comprising:

a container for holding waste, said container having a bottom surface, an exterior and substantially hollow interior;

a lid situated on top of said container, said lid having an upper surface and a lower surface;

a first port disposed along the upper surface of said lid enabling electrical communication between the exterior of said container and the interior of said container;

a second port disposed along the upper surface of said lid enabling fluid communication between the exterior of said container and the interior of said container;

a third port disposed along the upper surface of said lid enabling fluid communication between the exterior of said container and the interior of said container;

a fourth port disposed along the upper surface of said lid enabling fluid communication between the exterior of said container and the interior of said container;

a baffle fixably attached to the lower surface of said lid enabling deflection of waste to the bottom surface of said container;

a sensor disposed within said container and in electrical communication with said first port enabling determination of the amount of waste present within said container; and a conduit disposed within said container and in fluid communication with said fourth port enabling transportation of waste to the exterior of said container.

2. The apparatus of claim 1 further comprising a second sensor disposed within said container and in electrical communication with said second port enabling determination of the amount of waste present within said container.

3. The apparatus of claim 2 wherein said second sensor further comprises a vacuum safety float assembly and said second port further comprises a vacuum outlet port.

4. The apparatus of claim 1 wherein said container further comprises a vacuum canister.

5. The apparatus of claim 1 wherein said lid is removable from said container.

6. The apparatus of claim 1 wherein said first port further comprises a waste level switch fitting.

7. The apparatus of claim 1 wherein said second port further comprises a vacuum outlet port.

8. The apparatus of claim 1 wherein said third port further comprises a waste inlet port.

9. The apparatus of claim 1 wherein said fourth port further comprises a waste outlet port.

10. The apparatus of claim 1 wherein said baffle further comprises a baffle plate.

11. The apparatus of claim 10 wherein said baffle further comprises a waste inlet discharge shell and a waste inlet discharge tube in fluid communication with said third port.

12. The apparatus of claim 1 wherein said sensor further comprises a waste level switch assembly.

13. The apparatus of claim 1 wherein said conduit further comprises a waste outlet tube.

14. An improved vacuum receptacle comprising:

a vacuum canister, said vacuum canister having a bottom surface, an exterior and substantially hollow interior;

a removable lid situated on top of said vacuum canister, said lid having an upper surface and a lower surface;

a waste level switch fitting disposed along the upper surface of said lid enabling electrical communication between the exterior of said vacuum canister and the interior of said vacuum canister;

a vacuum outlet port disposed along the upper surface of said lid enabling fluid communication between the exterior of said vacuum canister and the interior of said vacuum canister;

a waste inlet port disposed along the upper surface of said lid enabling fluid communication between the exterior of said vacuum canister and the interior of said vacuum canister;

a waste outlet port disposed along the upper surface of said lid enabling fluid communication between the exterior of said vacuum canister and the interior of said vacuum canister;

a waste inlet discharge tube fixably attached to the lower surface of said lid and in fluid communication with said waste inlet port enabling deflection of waste to the bottom surface of said vacuum canister;

a waste inlet discharge shell fixably attached to the lower surface of said lid enabling deflection of waste to the bottom surface of said vacuum canister;

a baffle plate fixably attached to the lower surface of said lid enabling deflection of waste to the bottom surface of said vacuum canister;

a waste level switch assembly disposed within said vacuum canister and in electrical communication with said waste level switch fitting enabling determination of the amount of waste present within said vacuum canister;

a waste outlet tube disposed within said vacuum canister and in fluid communication with said waste outlet port enabling transportation of waste to the exterior of said vacuum canister; and a vacuum safety float assembly sensor disposed within said container and in electrical communication with said vacuum outlet port enabling determination of the amount of waste present within said vacuum canister.

15. An improved method of dental waste disposal comprising the steps of:

a) providing a vacuum receptacle comprising:

a vacuum canister, said vacuum canister having a bottom surface, an exterior and substantially hollow interior;

a removable lid situated on top of said vacuum canister, said lid having an upper surface and a lower surface;

a waste level switch fitting disposed along the upper surface of said lid enabling electrical communication between the exterior of said vacuum canister and the interior of said vacuum canister;

a vacuum outlet port disposed along the upper surface of said lid enabling fluid communication between the exterior of said vacuum canister and the interior of said vacuum canister;

a waste inlet port disposed along the upper surface of said lid enabling fluid communication between the exterior of said vacuum canister and the interior of said vacuum canister;

a waste outlet port disposed along the upper surface of said lid enabling fluid communication between the exterior of said vacuum canister; and the interior of said vacuum canister;

a waste inlet discharge tube fixably attached to the lower surface of said lid and in fluid communication with said waste inlet port enabling deflection of waste to the bottom surface of said vacuum canister;

a waste inlet discharge shell fixably attached to the lower surface of said lid enabling deflection of waste to the bottom surface of said vacuum canister;

a baffle plate fixably attached to the lower surface of said lid enabling deflection of waste to the bottom surface of said vacuum canister;

a waste level switch assembly disposed within said vacuum canister and in electrical communication with said waste level switch fitting enabling determination of the amount of waste present within said vacuum canister;

a waste outlet tube disposed within said vacuum canister and in fluid communication with said waste outlet port enabling transportation of waste to the exterior of said vacuum canister; and a vacuum safety float assembly sensor disposed within said container and in electrical communication with said vacuum outlet port enabling determination of the amount of waste present within said vacuum canister; and b) applying vacuum force to said vacuum outlet port, thereby drawing dental waste through said waste inlet port and into said vacuum canister, whereby upon accumulation of dental waste to a predetermined level within said vacuum canister, said waste level switch assembly activates a discharge pump external to said vacuum canister, thereby drawing fluid waste through said waste outlet port via said waste outlet tube.

* * * * *